United States Patent [19]

Jackson

[11] Patent Number: 4,785,658
[45] Date of Patent: Nov. 22, 1988

[54] METHOD AND APPARATUS FOR SENSING HYDROCARBON GASES

[76] Inventor: John Jackson, 1401 E. Girard Ave., Englewood, Colo. 80110

[21] Appl. No.: 803,604
[22] Filed: Dec. 2, 1985
[51] Int. Cl.$^4$ ............................................ G01N 31/00
[52] U.S. Cl. ...................................................... 73/23
[58] Field of Search ................... 73/432 R, 23, 864.34, 73/864.73, 864.81; 250/338.5 GA, 256, 343; 340/634

[56] References Cited

U.S. PATENT DOCUMENTS

| Re. 31,122 | 1/1983 | Fertl et al. | 73/152 |
|---|---|---|---|
| 2,879,663 | 3/1959 | Thomas | 250/343 |
| 3,107,517 | 10/1963 | Loyd et al. | 73/23 |
| 3,143,648 | 8/1964 | Bradley et al. | 250/338 GA |
| 3,333,458 | 8/1967 | Heath et al. | 73/23 |
| 3,399,398 | 8/1968 | Becker et al. | 73/27 R |
| 3,444,721 | 5/1969 | Hearn et al. | 73/23 |
| 3,734,489 | 5/1973 | Milly | 73/23 |
| 3,947,683 | 3/1976 | Schultz et al. | 250/270 |
| 4,064,436 | 12/1977 | Ward, III | 250/253 |
| 4,065,972 | 1/1978 | Holub et al. | 73/864.52 |
| 4,071,755 | 1/1978 | Supernaw et al. | 250/256 |
| 4,156,138 | 5/1979 | Felice | 250/253 |
| 4,185,491 | 1/1980 | Owen | 340/634 |
| 4,187,908 | 2/1980 | Fertl et al. | 73/152 |
| 4,327,361 | 4/1982 | Berlin | 340/634 |
| 4,412,444 | 11/1983 | Ketel, II | 73/23 |
| 4,446,718 | 5/1984 | Bukowiecki et al. | 340/634 |

FOREIGN PATENT DOCUMENTS 2151796 7/1985 United Kingdom .................... 73/23

Primary Examiner—Stewart J. Levy
Assistant Examiner—Robert R. Raevis
Attorney, Agent, or Firm—Fields, Lewis, Pittenger & Rost

[57] ABSTRACT

A tubular housing is provided with a conductance sensitive gas detector. Air is drawn by a fan through the housing at a constant rate as the gas detector is traversed across a land area to be studied for reservoirs of hydrocarbon material. The detector is attached to the outside of the vehicle. An output signal from an oscillator whose output frequency varies in response to changes in resistance across two spaced electrodes in the sensor is provided to a recorder within the vehicle. The output frequency is correlated with parts per million of hydrocarbon gas so that meaningful reading can be obtained. An RC timing network with a parallel resistance arrangement with the electrodes provides large changes in oscillator frequency in response to small changes in resistance across the plates.

4 Claims, 3 Drawing Sheets

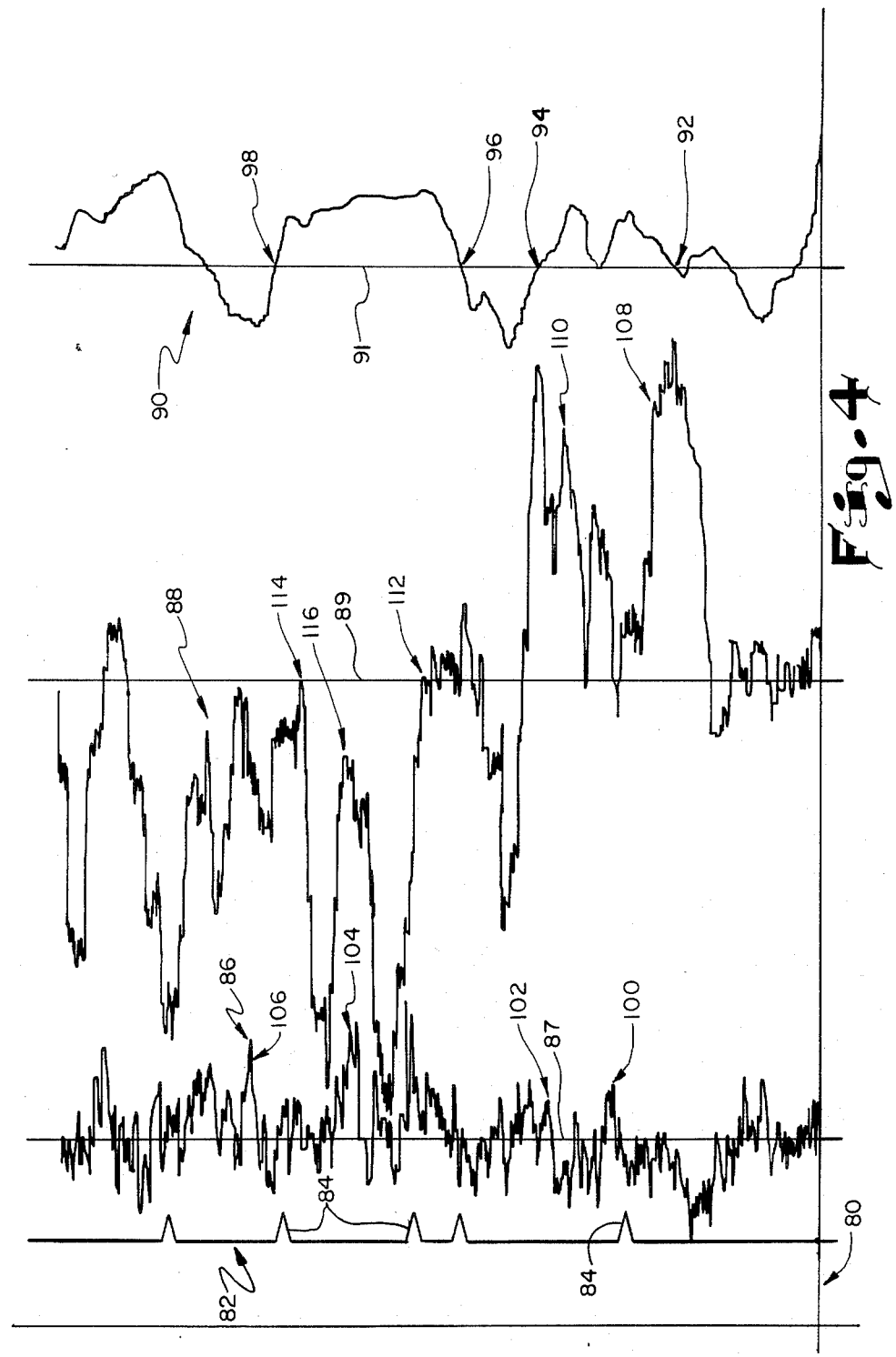

METHOD AND APPARATUS FOR SENSING HYDROCARBON GASES

TECHNICAL FIELD

This invention relates to a method and apparatus for locating a subterranean reservoir of hydrocarbon material and more particularly to a method utilizing a gas sniffer of the type which is moved along the surface of the land area under investigation.

BACKGROUND ART

It is known in the prior art to bury inverted cups in a prearranged array for collecting gases for analyzing ore bodies or reservoirs of hydrocarbon material such as oil or natural gas under a predefined land area. In this regard, U.S. Pat. No. 4,065,972 to Holub, et al. discloses attaching any number of gas detectors to the inside bottom of plastic drinking cups. The patent discloses various devices for detecting underground minerals such as oil, gas, coal, water and other resources. These cups are buried in the earth at varying depths and left for a period of time for collecting specified gases that migrate from the underground mineral body through the earth and into the respective cups. After collection, the collecting element in each cup is analyzed, such as by conducting a conventional atomic adsorption analysis.

U.S. Pat. No. 4,156,138 to Felice discloses suspending an alpha-sensitive dosimeter in an inverted cup between the bottom and open end to absorb alpha-radiation.

U.S. Pat. No. 4,064,436 to Ward III discloses a radon detector which includes an inverted cup with a detection strip which is sensitive to radon gas and also includes a pervious membrane across the mouth of the cup.

The prior art methods, while being fairly reliable are quite time consuming since it is necessary to bury each of the cups individually; to mark their location; to come back at a subsequent time, such as 30 days, to retrieve the cups; and to analyze the amount of gas collected on a collecting substance in each cup. Thus, many weeks are involved in the process and much labor is required, thereby resulting in substantial cost in evaluating the ore body below a particular land area under investigation.

DISCLOSURE OF THE INVENTION

A method is provided for locating a subterranean reservoir of hydrocarbon material. This method involves attaching a sensor to a vehicle which is sensitive to migrating hydrocarbon gas and traversing the vehicle over a land area suspected of having a subterranean reservoir of hydrocarbon material. A readout is provided which is responsive to the hydrocarbon gas sensed and which is correlated to the distance traveled by the vehicle over the land area to establish the location of high concentrations of migrating hydrocarbon gas.

The apparatus for locating the subterranean hydrocarbon material includes a tubular housing which has an intake end and an outlet end and a constant speed fan mounted in the housing adjacent the inlet for drawing a constant supply of air through the housing. The sensor has a heater to maintain it at a preselected constant temperature. This sensor is mounted in the housing downstream of the fan for sensing migrating hydrocarbon gas and means is connected across spaced plates in the sensor which is responsive to changes in the resistance across the plates in response to the amount of hydrocarbon gas in the air passing through the housing to provide data which is indicative of the amount of hydrocarbon gas in the air.

More specifically, the method includes varying the oscillation rate of a frequency oscillator as a function of changes in the spaced plate resistance in response to hydrocarbon gas in the air directed past the sensor. The cycles per second are correlated to parts per million to obtain a reading of hydrocarbon gas concentration in the ambient air at any location in the land area over which the vehicle traverses. The current to the heater can be selectively varied to cause the sensor to be more sensitive to either light or heavy gases. In addition, the device can also sense total gamma count, sense gamma high energy, such as cobalt 60, and simultaneously produce a readout on a graph of the total gamma count, the total high energy, such as cobalt 60, and the hydrocarbon gas detected so that the respective readouts can be compared for correlations which indicates the existence of a subterranean reservoir of hydrocarbon material.

A rheostat can be provided on the heater circuit for selectively adjusting the current to the sensor to make it more sensitive to either heavy or light hydrocarbon gases. The higher the temperature of the heater, the more sensitive the sensor is to light gases. Conversely, the lower the temperature of the heater, the more sensitive the sensor is to heavy gases. Of course, a decrease in rheostat resistance will raise the heater temperature and an increase in rheostat resistance will decrease the heater temperature.

Baffles can be provided in the housing for mixing the air passing through the housing at the sensor to get a more reliable reading. In addition, means can be provided for correlating the distance traveled by the vehicle over the land area to establish the location of the high concentrations of the migrating hydrocarbon gas. A flexible hose can be attached to the housing at the inlet having an end positioned adjacent to the ground receiving ambient air which is drawn through the housing by the fan at constant speed and is not adversely effected by the speed or direction of the vehicle or by the wind.

Additional advantages of this invention will become apparent from the description which follows, taken in conjunction with the accompanying drawings.

BRIEF DESCRIPTION OF THE DRAWINGS

FIG. 4 is a reproduction of a graph chart showing the detection of hydrocarbon gases and other gases.

BEST MODE FOR CARRYING OUT THE INVENTION

Figure 1:
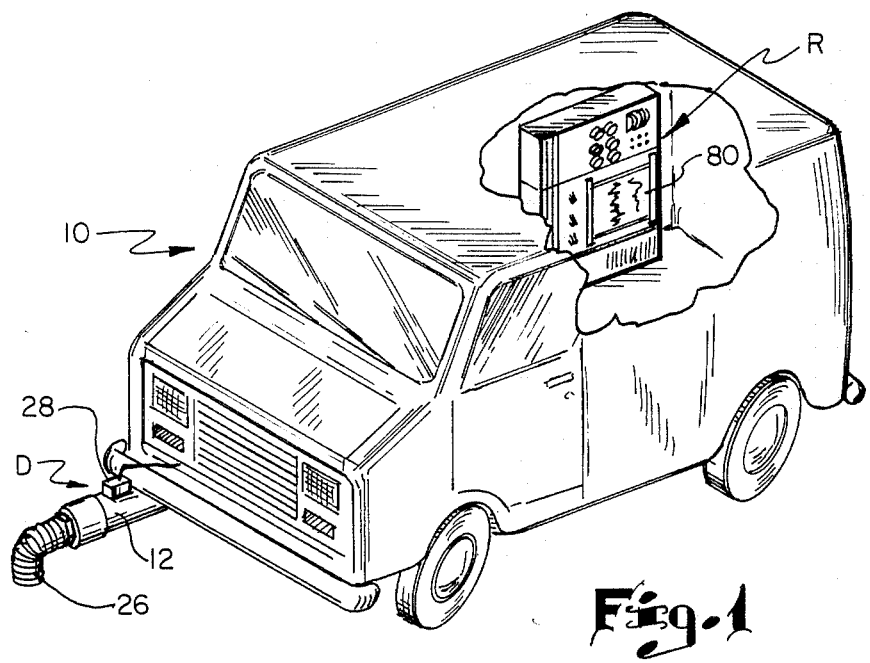
FIG. 1 is a perspective view of a vehicle utilizing the gas sensor of this invention, with parts being broken away to show further details of the invention.
Figure 2:
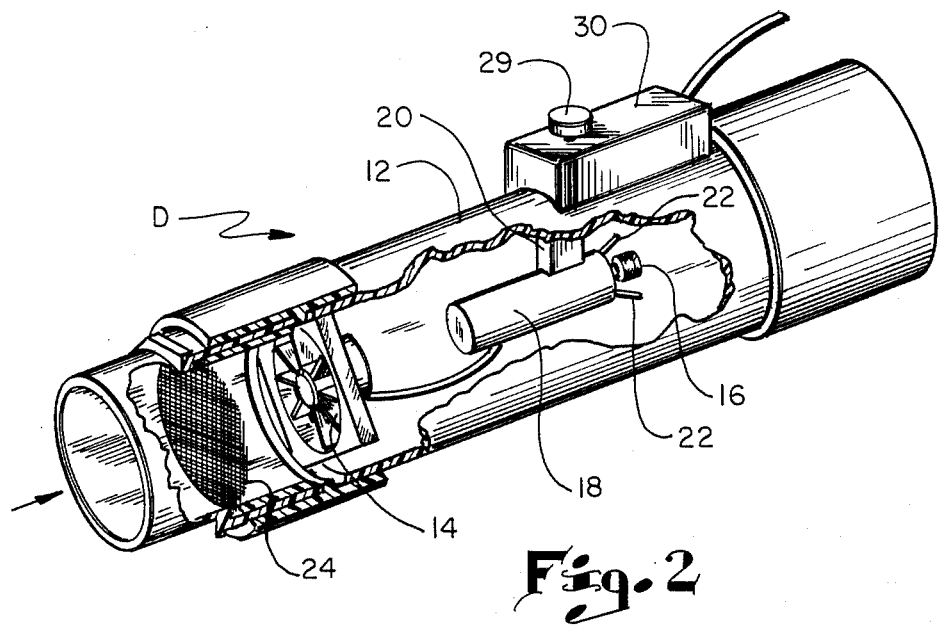
FIG. 2 is an enlarged view of the gas sensor of this invention with parts broken away for clarity of illustration.

In accordance with this invention, a gas detector D is mounted on a vehicle 10, such as by attachment to the bumper so that as the vehicle is driven across a land area, gas in the ambient air will be drawn through the detector and analyzed to provide a visible indicia on a recorder R which is mounted within the vehicle 10. Conveniently, the probe or detector has a tubular housing 12 which can be a piece of plastic pipe four and one half inches in diameter and 16 inches long. The pipe may be constructed of polyvinylchloride or any other suitable material. As seen in FIG. 2, a fan 14 is mounted adjacent the inlet of housing 12 and is driven at a constant rotational speed so that the flow of air through housing 12 is constant. A semiconductor gas sensor 16 is attached to a circuit module 18 which is mounted centrally within housing 12 by means of supports 20. A suitable sensor is the J4-807 sensor sold by GC Electronics of Rockford, Illinois. Baffles 22 are provided adjacent sensor 16 for creating turbulence in the air passing through the housing 12 so that the air reaching sensor 16 constitutes a good mixture of the ambient air being drawn through the housing. Advantageously, a screen 24 extends across the inlet end of housing 12 to prevent bugs, leaves and other foreign material from entering the housing. So that the rate of air flowing through housing 12 will be controlled solely by fan 14 and will not be effected by the speed at which the vehicle is driven or by wind conditions, a piece of flexible tubing 26, as seen in FIG. 1, is attached to the inlet end of housing 12 and hangs down toward the ground so that all air being drawn into the housing is drawn up from the bottom by fan 14. This facilitates establishing a stable base line signal or null line signal which is indicative of background gases in the land area under consideration. Variations in gas concentrations can then be measured, using this base line signal as a reference. It will be understood by one skilled in the art that the background level will differ from one locale to another and can be established by reference to available oil and gas charts, a general knowledge of the geological formations in the locale and the altitude of the locale.

Figure 3:
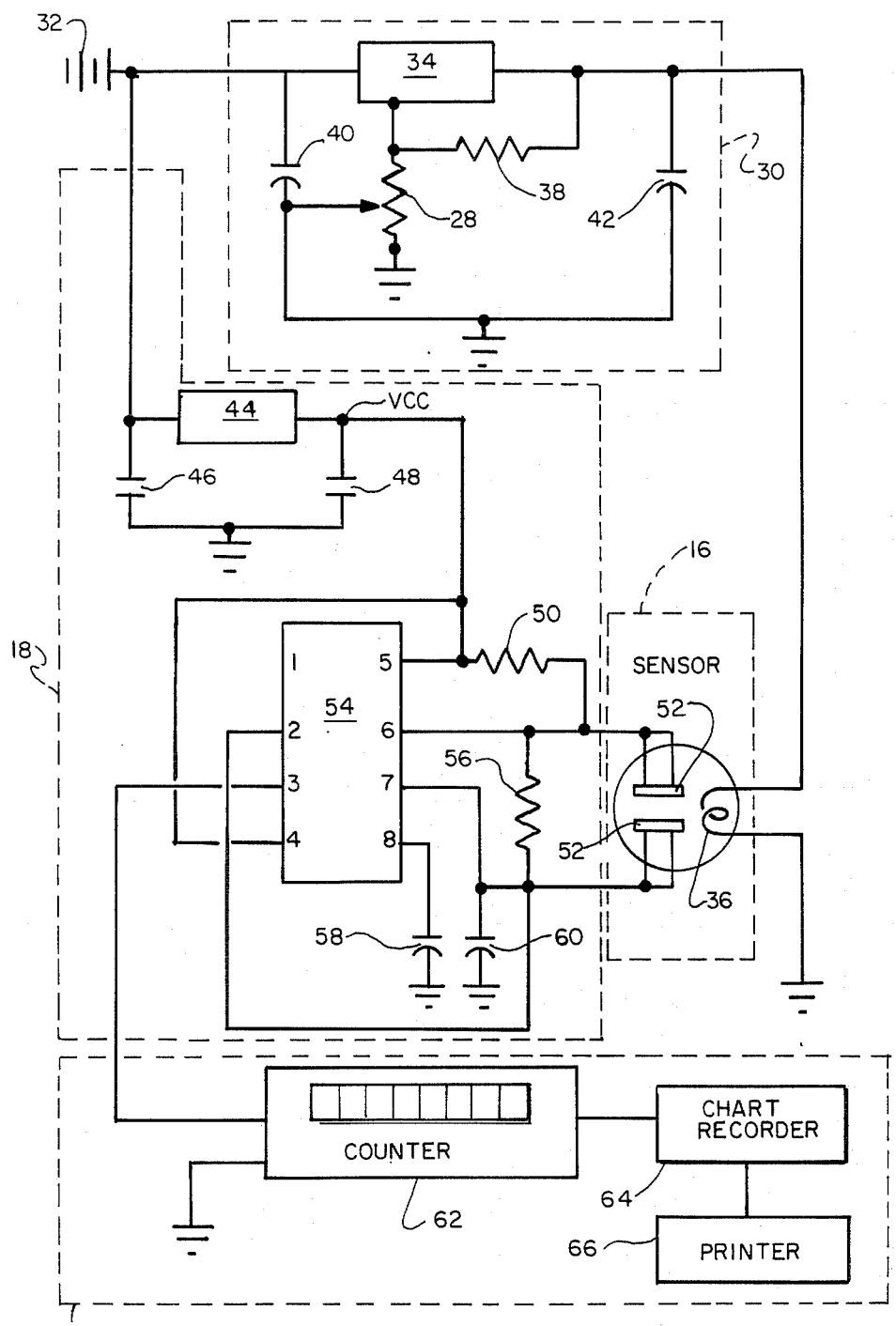
FIG. 3 is a circuit diagram of the gas sensor circuitry and recording apparatus.

Referring now to the circuit diagram of FIG. 3 there is shown a DC battery 32, preferably, 12 volts, that supplies electric power to the heater power supply 30 and to the circuit module 18. Conveniently, this battery is the battery of vehicle 10.

The heater power supply 30 has a power device 34 with an input connected to a D.C. power supply, such as battery 32 and an output connected to the heater coil 36 of the sensor. A rheostat 28 is connected to device 34 so that adjustment of the slide contact of the rheostat by turning knob 29 changes the current to the heater coil 36. This adjustment makes the sensor more sensitive to either light gases or heavy gases. A resistor 38 is connected between the high side of the rheostat and the output of device 34. A filter capacitor 40 is connected to the side contact of the rheostat and between the input of device 34 and ground and a filter capacitor 42 is connected between the output of device 34 and ground. The filter capacitors 40 and 42 stabilize D.C. power supply 32. This heater power supply 30 provides a very precise variable power to the heater coil 36 that is heavily filtered as well as stabilized.

The circuit module 18 is shown to include a power device 44 with a filter capacitor 46 between the input and ground and a filter capacitor 48 between the output and ground. This circuit reduces the voltage of the battery to a suitable lower DC voltage such as +5 VDC which is designated VCC and is used as a bias voltage for the circuits hereinafter described.

The circuit module 18 is further shown to include a frequency oscillator using a timer device 54. In this circuit a load resistor 50 is connected in series with the electrodes 52 of sensor 16 to a terminal of the timer device 54.

An RC timing network for the frequency oscillator includes a resistor 56 and capacitor 60 connected to terminals of device 54 with the electrodes 52 of sensor being connected across resistor 56 in parallel. The frequency of oscillations then is determined by the parallel arrangement of resistors 56 and electrodes 52 in series with capacitor 60. The resistance of electrodes 52 changes in relation to the gas concentration sensed. The resistance of the electrodes 52 is considerably smaller than the resistance of resistor 56 to provide a high degree of sensitivity with the frequency of oscillations of the oscillator circuit varying in relation to the concentration of the gas being measured. Typically, the resistance of the electrodes 52 would be 30K ohms, resistor 56 would be 100K ohms and capacitor 60 would 0.02 $\mu f$.

This timer device receives the bias voltage VCC and has a capacitor 58 connected to another terminal. This frequency oscillator produces oscillations over a range of frequencies. The frequency changes greatly in response to small changes in the resistance of the electrode 52, which is a measure of the gas present. The output frequency is provided to output terminal 3. The rate of oscillations is read by a counter 62 and is correlated to the PPM of the gas being tested. The output of the counter 62 can be recorded on a chart recorder 64 and then in a printer 66 for a permanent record if desired.

By way of illustration only and not by way of limitation, listed below are devices which have been found suitable for use in the above-described electrical circuit.

| DEVICE | PART NO. | MANUFACTURER |
|---|---|---|
| Power Device 34 | LM317 | National Semiconductor |
| Power Device 44 | M8L05 | Motorala |
| Timer Device 54 | LF555 | National Semiconductor |

A typical chart 80 is shown in FIG. 4. The graph 82 at the left-hand side of chart 80 depicts the distance traveled by the vehicle, with each peak 84 thereon representing 0.1 miles. The next graph 86 represents a response to the presence of gamma high energy, such as cobalt 60 which is obtained by other apparatus.

The graph includes a base line 87 which represents a predefined background level of radiation. The move of graph 86 to the right indicate increased levels of gamma high energy while swings of the graph to the left indicate lower levels of gamma high energy. Graph 88 depicts a standard graph for total count of gamma radiation, which is also created by other apparatus. This graph has a base line 89 as a reference. When graph 88 moves to the right it indicates an increase in total count of gamma, and a swing to the left indicates a decrease in total count of gamma. In other words, as a vehicle traverses across a land surface many factors can affect the readings, such as: it may be traversing a field in which fertilizer has been placed; it may traverse an oil or asphalt road which would shift the base line 87 and 89 of the gamma portion of FIG. 4. Wind speed and direction may change; other vehicles may pass by; or other variations in the terrain which may affect the ambient gas detected.

Graph 90 depicts readings obtained by the use the apparatus disclosed herein. Base line 91 of this graph represents a base for background levels of gas present over the surface of the earth. Any swings of graph 90 to the right of the base line indicates gas levels above the base line amounts, and swings of the graph to the left of the base line indicates levels of gas below base line amounts. In graph 90, as depicted, there are areas indicating gas levels above normal background gas levels. Two examples are the portions of the graph between arrows 92 and 94 and between arrows 96 and 98, respectfully. In accordance with the method of this invention, the actual presence of a subterranean hydrocarbon reserve can be confirmed by referring back to graphs 86 and 88. In graph 86, it will be noted that between arrows 100 and 102 there is a drop off in gamma high energy. Also, between arrows 108 and 110 of graph 88 there is also a drop off in total; count gamma radiation. Thus, these two graphs confirm graph 90 and therefore confirm to the observer that there is a high likelihood that substantial reverses of hydrocarbon materials will be found in this location.

Graph 90 also indicates, between arrows 96 and 98, the presence of significant gas. It gas is present, this should correlate to low levels of gamma high energy and total count gamma radiation in graphs 96 and 98. In graph 86 we see that between arrows 104 and 106 the gamma high energy does in fact drop off. Similarly, in graph 88 we see a drop off in gamma total count between arrows 112 and 114. These is a spike to the right between arrows 112 and 114 at arrow 116. However, this represents a surface change in the earth. In the absence of the use of graph 90 of this invention, the presence of hydrocarbon reserves at this location probably would be overlooked because of this surface change. Thus, the present invention minimizes the possibility that significant hydrocarbon reserves will be missed.

To correlate the oscillator frequency to PPM, the device will be calibrated under precisely controlled conditions. The frequency of the oscillator will be observed under normal background conditions. Then air will be passed through the sensor which contains known PPM of hydrocarbon gas and the changes in frequency noted.

From the foregoing, the advantages of this invention are readily apparent. By use of the present invention, readings may be taken rapidly over a land area under consideration by use of the gas detector of this invention which can be attached to the bumper or other portion of a vehicle. A reading is obtained on a chart which can be compared with readings by other known methods to verify location of gas and can be correlated with the distance traveled by the vehicle to determine the exact location of the hydrocarbon reservoir. In addition, by controlling the current to the heater coil of the sensor, the device may be set to be more sensitive to heavy gases or alternatively to be more sensitive to light gases. Thus, it can be determined more easily whether or not the hydrocarbon reservoir is a gas field or an oil reservoir.

An important novel feature of the invention is the use of the change in resistance of the electrodes of the gas detector to vary the output frequency of an oscillator which can be correlated to parts per million to provide a reading of gas concentrations.

Alternately the device could be used in vehicles other than land vehicles, such as in an aircraft wherein the gas detector D would be attached to a boom which would be lowered from the aircraft to a position near the ground as the aircraft flies over the land area under investigation.

Additionally, the probe can be hand held and used independently of the vehicle. In this usage, the inlet would be placed sequentially in each of several one foot deep holes for several minutes to provide readings of soil gas buildup.

This invention has been described in detail with reference to a particular embodiment thereof, but it will be understood that various other modifications can be effected within the spirit and scope of this invention.

I claim:

1. A method of locating a subterranean reservoir of hydrocarbon material, said method comprising the steps of: is
    attaching a sensor to a vehicle so that the sensor adjacent the ground, which sensor is sensitive to migrating hydrocarbon gas in the ambient air;
    traversing the vehicle over a land area suspected of having the subterranean reservoir of hydrocarbon material;
    sensing total gamma count;
    sensing gamma high energy:
    sensing hydrocarbon gas in the ambient air with the sensor;
    simultaneously producing a readout on a graph of the total gamma count, the gamma high energy and the hydrocarbon gas;
    comparing the respective readouts for total gamma count, gamma high energy and hydrocarbon gas which indicate the existence of the subterranean reservoir of hydrocarbon material, which is correlated to the distance traveled by the vehicle over the land area to establish the location of high concentrations of migrating hydrocarbon gas.

2. A method, as claimed in claim 1, including the further steps of:
    providing a tubular housing around the sensor, which housing is open to the atmosphere at both ends; and
    directing ambient air through the housing and past the sensor at a constant rate to establish a base line signal which is indicative of the level of background hydrocarbon gas.

3. A method, as claimed in claim 2, wherein the sensor is a conductive sensitive sensor having a heater coil and spaced electrodes adjacent thereto which are connected to a D.C. voltage source, said method comprising the further steps of:
    varying the frequency rate of a frequency oscillator, the resistance of the sensor being responsive to the frequency rate of the oscillator;
    converting the frequency rate to cycles per second; and
    correlating cycles per second to parts per million to obtain a reading of hydrocarbon gas concentration in the ambient air at any location on the land area over which the vehicle traverses.

4. A method, as claimed in claim 3, including the further step of:
    varying the D.C. voltage to the heater coil to make the sensor more sensitive to either light or heavy gases.

* * * * *